United States Patent [19]
Aebischer et al.

[11] Patent Number: 5,487,739
[45] Date of Patent: Jan. 30, 1996

[54] IMPLANTABLE THERAPY SYSTEMS AND METHODS

[75] Inventors: Patrick Aebischer, Barrington; Moses Goddard, Tiverton, both of R.I.; John G. Moldauer, Brooklyn; Paul J. Mulhauser, New York, both of N.Y.; Anne M. Rathbun, Providence, R.I.; Paul R. Sanberg, Greenwich, R.I.; Alfred V. Vasconcellos, Cranston, R.I.; Nicholas F. Warner, Belmont, Mass.

[73] Assignee: Brown University Research Foundation, Providence, R.I.

[21] Appl. No.: 459,815

[22] Filed: Jun. 2, 1995

Related U.S. Application Data

[63] Continuation of Ser. No. 998,368, Dec. 30, 1992, abandoned, which is a continuation-in-part of Ser. No. 722,947, Jun. 28, 1991, abandoned, which is a continuation-in-part of Ser. No. 369,296, Jun. 19, 1989, abandoned, which is a continuation-in-part of Ser. No. 121,626, Nov. 17, 1997, Pat. No. 4,892,538.

[30] Foreign Application Priority Data

Jun. 25, 1992 [WO] WIPO ............... PCT/US92/05369

[51] Int. Cl.[6] ............................................ A61K 9/22
[52] U.S. Cl. ............... 604/890.1; 604/93; 604/164; 604/265; 424/424
[58] Field of Search ............... 604/93, 116, 117, 604/59, 60, 890.1, 892.1, 84, 285, 403, 164, 170, 264, 265, 53; 606/150; 424/424; 623/11, 12

[56] References Cited

U.S. PATENT DOCUMENTS 3,093,831  6/1963  Jordan et al. .................... 3/1

(List continued on next page.)

FOREIGN PATENT DOCUMENTS 0147939  7/1985  European Pat. Off. .
0213908  8/1986  European Pat. Off. .

(List continued on next page.)

OTHER PUBLICATIONS

Tresco et al. (1992) ASAIO Journal 38:17–23.
Aebisher et al. (1991) Science 252:133.
Winn et al. (1991) Experimental Neurology 113:322–329.

(List continued on next page.)

*Primary Examiner*—C. Fred Rosenbaum
*Assistant Examiner*—Mark Bockelman
*Attorney, Agent, or Firm*—Fish & Neave; Ivor R. Elrifi; Barbara A. Ruskin

[57] ABSTRACT

Implantable therapy systems are disclosed for the local and controlled delivery of a biologically active factor to the brain, spinal cord and other target regions of a subject suffering from a debilitating condition. The method of the invention involves surgically exposing an insertion site, generally located above a predetermined treatment site (12), in a patient. A cannula (20), having an obturator (30) or dilator (104) positioned therein, is inserted at the insertion site, defining a pathway to the treatment site. In some instances, the cannula can be inserted along the path of a guidewire (102) previously positioned at the treatment site. The cannula (20) is preferably a low friction polymeric material such as polytetrafluoroethylene. The cannula (20) generally has an open proximal end for receiving the obturator (30) or dilator (104), and an open distal end, preferably a tapered end, for delivery of neurologically active factors to the treatment site (12). The obturator (30) is then removed from the cannula (20), and a biocompatible tethered vehicle (40) containing a biologically active material is inserted into the cannula along the passageway. A pusher can be inserted within the cannula, behind the vehicle (40), to position the proximal end of the vehicle at the distal end of the cannula (20b). Once the vehicle (40) is positioned near the distal end of the cannula (20), the cannula is removed from the passageway, followed by the pusher, leaving the vehicle (40) positioned at the treatment site (12).

20 Claims, 10 Drawing Sheets

U.S. PATENT DOCUMENTS

| | | | |
|---|---|---|---|
| 3,583,387 | 6/1971 | Garner | 604/118 |
| 3,640,269 | 2/1972 | Delgado | 604/93 |
| 3,911,911 | 10/1975 | Scommegna | 424/432 |
| 4,241,187 | 12/1980 | White | 435/284 |
| 4,298,002 | 11/1981 | Ronel et al. | 623/11 |
| 4,309,776 | 1/1982 | Berguer | 424/424 |
| 4,352,883 | 11/1982 | Lim | 11/10 |
| 4,378,016 | 3/1983 | Loeb | 128/260 |
| 4,391,909 | 7/1982 | Lim | 11/10 |
| 4,402,694 | 9/1983 | Ash et al. | 604/891 |
| 4,451,253 | 5/1984 | Harman | 604/60 |
| 4,479,796 | 10/1984 | Kallok | 604/60 |
| 4,578,057 | 3/1986 | Sussman | 604/167 |
| 4,619,644 | 10/1986 | Scott | 604/53 |
| 4,686,098 | 8/1987 | Kopchick et al. | 424/424 |
| 4,767,400 | 8/1988 | Miller et al. | 604/264 |
| 4,850,975 | 7/1989 | Furukawa | 604/53 |
| 4,892,538 | 1/1990 | Aebisher et al. | 604/891 |
| 4,902,295 | 2/1990 | Waltham et al. | 623/11 |
| 4,931,056 | 6/1990 | Ghajar et al. | 604/174 |
| 4,941,874 | 7/1990 | Sandow et al. | 604/60 |
| 4,960,415 | 10/1990 | Reinmuller | 604/890.1 |
| 4,973,304 | 11/1990 | Graham et al. | 604/48 |
| 4,976,670 | 12/1990 | Franetzki et al. | 604/265 |
| 4,994,027 | 2/1991 | Farrell | 604/53 |
| 5,004,457 | 4/1991 | Wyatt et al. | 604/117 |
| 5,106,627 | 4/1992 | Aebisher et al. | 604/890.1 |
| 5,125,888 | 6/1992 | Howard et al. | 604/890.1 |
| 5,139,486 | 8/1992 | Moss | 604/164 |
| 5,158,544 | 10/1992 | Weinstein | 604/53 |
| 5,292,515 | 3/1994 | Moro et al. | 604/59 |

FOREIGN PATENT DOCUMENTS

| | | |
|---|---|---|
| 0304700 | 8/1988 | European Pat. Off. |
| 2564734 | 3/1984 | France |
| 2130916 | 6/1984 | United Kingdom |
| WO84/00304 | 2/1984 | WIPO |
| WO87/03802 | 7/1987 | WIPO |
| WO88/10103 | 12/1988 | WIPO |
| WO89/04655 | 6/1989 | WIPO |
| WO91/00119 | 10/1991 | WIPO |
| WO92/13501 | 8/1992 | WIPO ... A61F 2/04 |

OTHER PUBLICATIONS

Aebisher et al. (1991) Brian Research 560:43–49.

Aebisher et al. (1991) Experimental Neurology 111:269–275.

Aebisher et al. (1991) J. Biomech. Engineering 113:178–183.

Aebisher et al. (1991) Biomaterials 12:50–56.

Jaeger et al. (1991) Brian Research 551:163–170.

Hoffman et al. (1990) Experimental Neurology 110:39–44.

Winn et al. (1989) Experimental Neurology 105:244–250.

Winn et al. (1989) J. Biomed. Mater. Res. 23:31–44.

Aebisher et al. (1988) Brian Research 448:364–368.

Jaeger et al. (1990) Progress In Brain Research 82:41–46.

Bjorklund et al. (1982) Nature 298:652–654.

Brundin et al. (1985) Experimental Brain Research 60:204–208.

Calne et al. (1969) The Lancet Nov. 8, pp. 973–976.

Calne et al. (1974) British Medical Journal Nov. 23, pp. 442–444.

M. A. Dichter (1983) Principal of Internal Medicine pp. 2018, 2119–2132.

Freed et al. (1981) Nature 292:351.

Hefti et al. (1985) Brain Research 348:283–288.

Perlow et al. (1979) Science 204:643–647.

Stenaas and Stenaas, (1978) ACTA Neuropath. 41:145–155.

Sun et al. (1977) Diabetes 26:1136–1139.

Sagen et al., "Adrenal Medullary Transplants Increase Spinal Cord Cerebrospinal Fluid Catecholamine Levels and Reduce Pain Sensitivity," Journal of Neurochemistry, vol. 56, No. 2, pp. 623–627 (1991).

Sagen et al., "Increased Levels of Met–enkephalin–like Immunoreactivity in the Spinal Cord CSF of Rats with Adrenal Medullary Transplants," *Brain Research*, 502, pp. 1–10 (1989).

Sagen et al., "Adrenal Medullary Tissue Transplants in the Rat Spinal Cord Reduce Pain Sensitivity," *Brain Research*, 384, pp. 189–194 (1986).

Sagen et al., "Analgesia Induced by Isolated Bovine Chromaffin Cells Implanted in Rat Spinal Cord," Neurobiology, vol. 83, pp. 7522–7526 (1986).

Sagen et al., "Fine Structure of Adrenal Medullary Grafts in the Pain Modulatory Regions of the Rat Periaqueductal Gray," Experimental Brain Research, pp. 380–390 (1987).

Sagen et al., "Monoaminergic Neural Transplants Prevent Learned Helplessness in a Rat Depression Model," Society of Biological Psychiatry, vol. 28, pp. 1037–1048 (1990).

Sagen et al., "Proloned Analgesia by Enkephalinase Inhibition in Rats With Spinal Cord Adrenal Medullary Transplants," European Journal of Pharmacology, vol. 179, pp. 427–433 (1990).

Pezzoli et al., "Non–chromaffin Tissue Plus Nerve Growth Factor Reduces Experimental Parkinsonism in Aged Rats," *Brain Research*, vol. 459, pp. 398–403 (1988).

Tze et al., "Xenotransplantation of Rat Pancreatic Endocrine Cells in Spontaneous and Streptozotocin–induced Diabetic Monkeys," Translation Proceedings, vol. 21, No. 1, pp. 2736–2738 (1989).

Stark et al., "Enhanced Antinociception by Adenosinergic Agonists in Rats With Adrenal Medullary Transplants in the Spinal Subarachnoid Space," Society of Neuroscience Abstracts, vol. 17, 99.4 (1991) Abstract Only.

Hama et al., "Adrenal Medullary Transplants Reduce Pain in Rats With Experimental Painful Peripheral Neuropathy," Society for Neuroscience Abstracts, vol. 17, 99.6 (1991) Abstract Only.

Sagen et al., "Pain Recuction by Adrenal Medullary Transplants in the Spinal Subarachnoid Space of Terminal Cancer Patients," Society for Neuroscience Abstracts, vol. 17, 99.1 (1991) Abstract Only.

Wang et al., "Pain Reduction by Transplants of Polymer Encapsulated Bovine Chromaffin Cells in the Rat Spinal Subarachnoid Space," Society for Neuroscience Abstracts, vol. 17, 99.5 (1991).

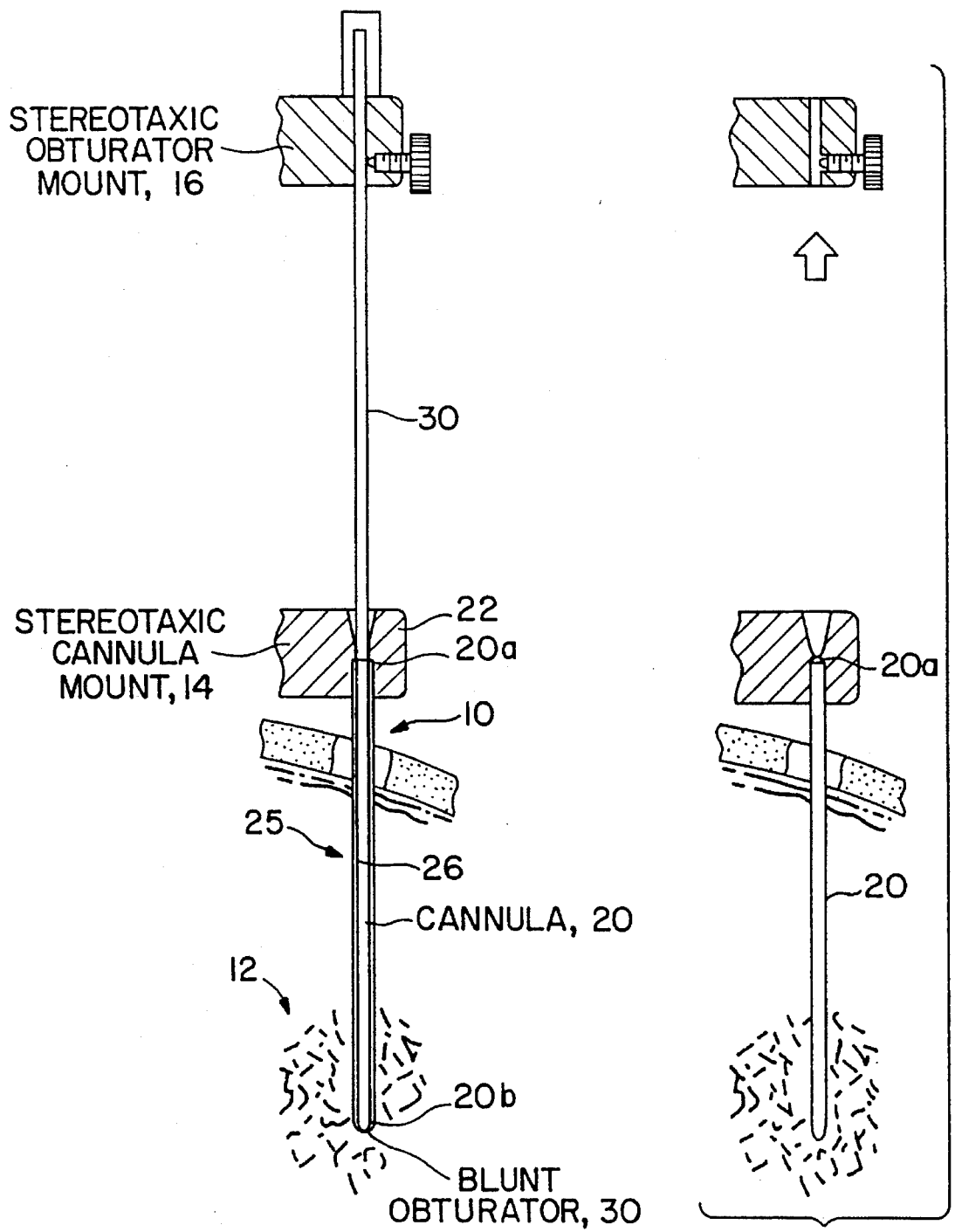

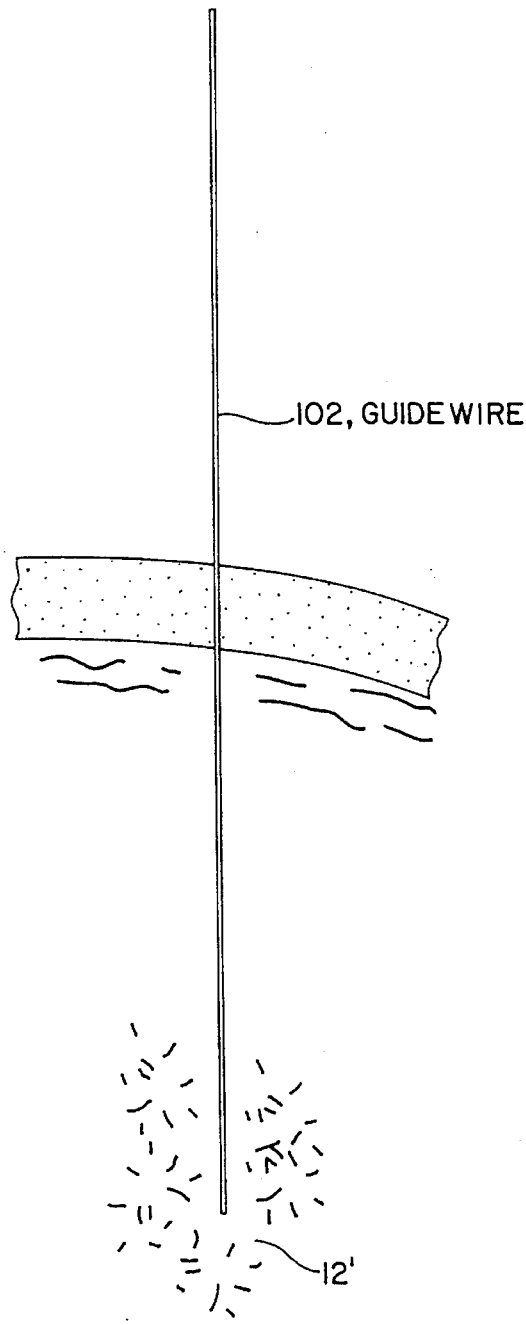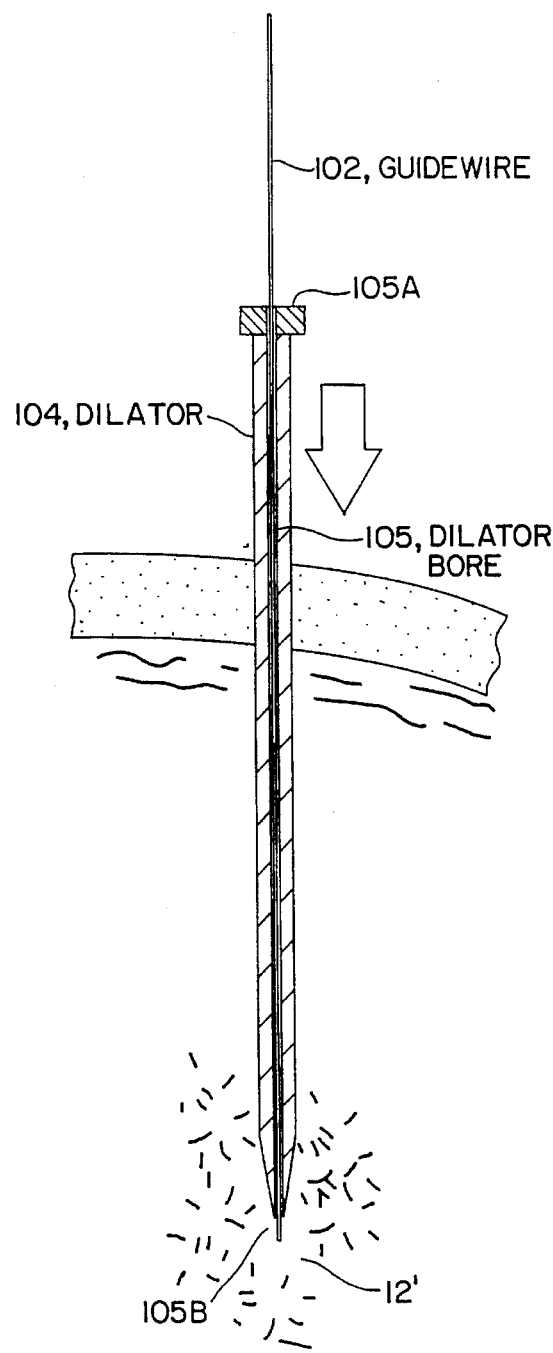
FIG. 2C
FIG. 2D

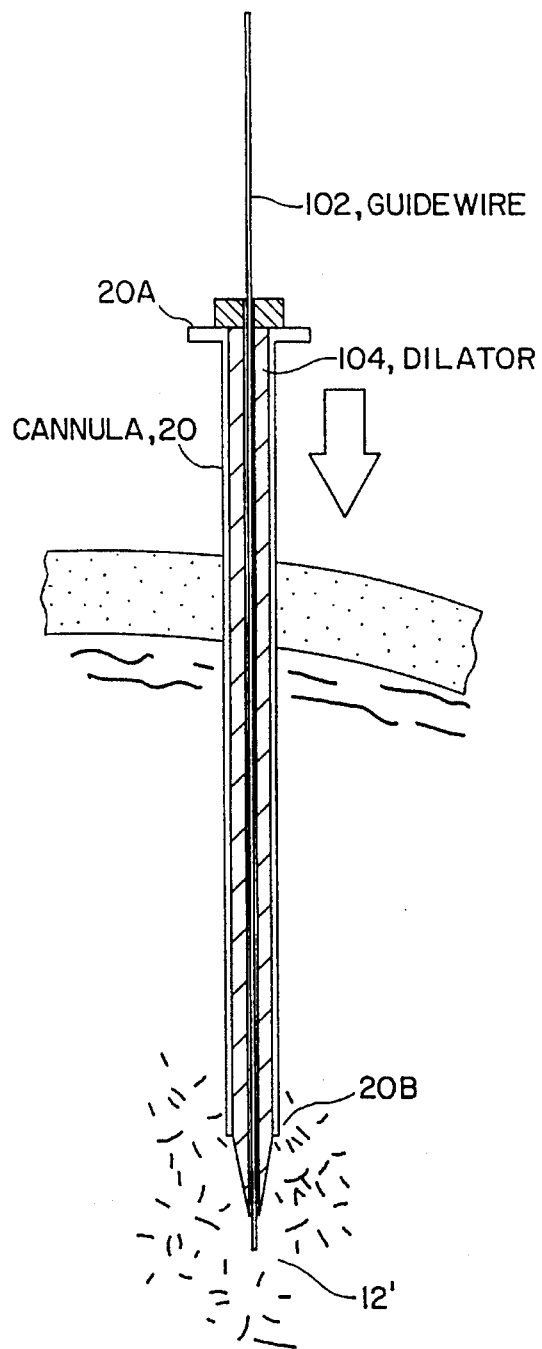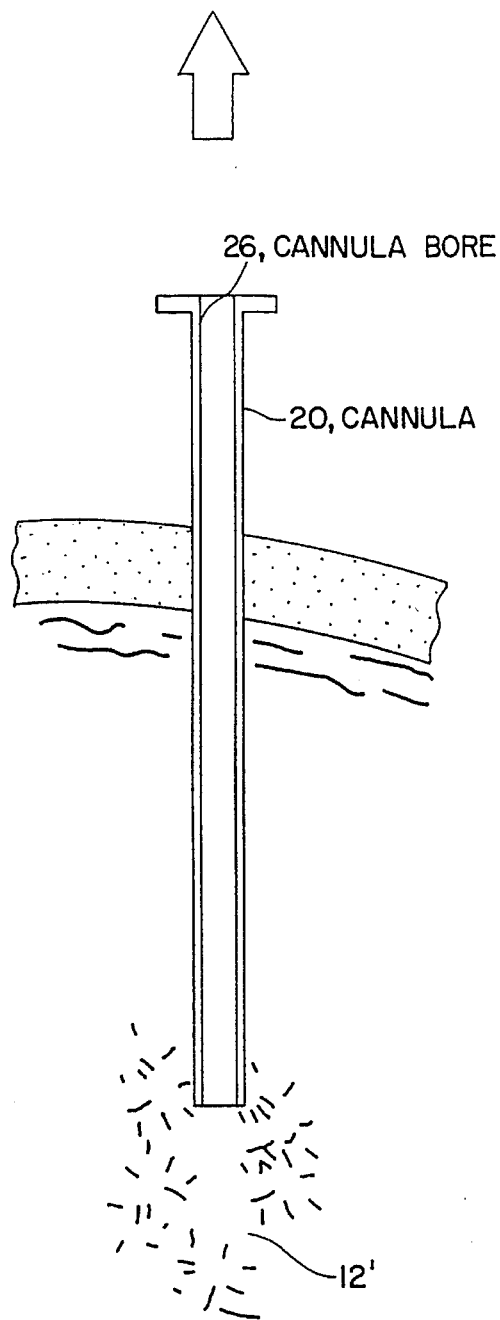
FIG. 2E
FIG. 2F

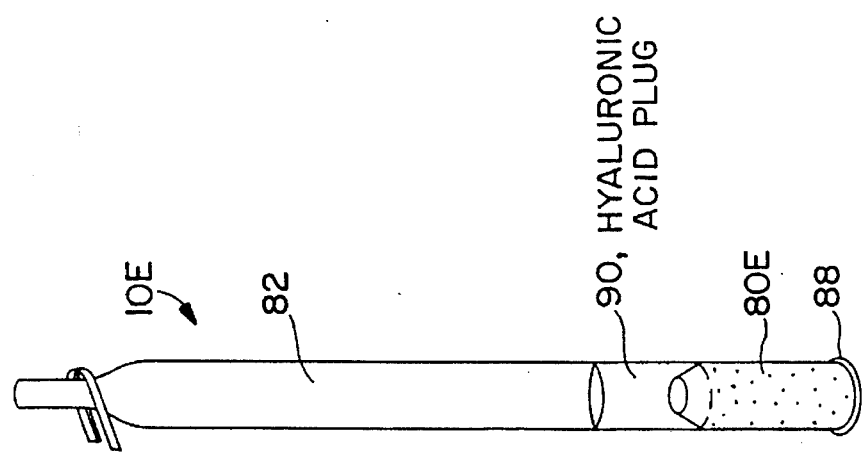
FIG. 3E
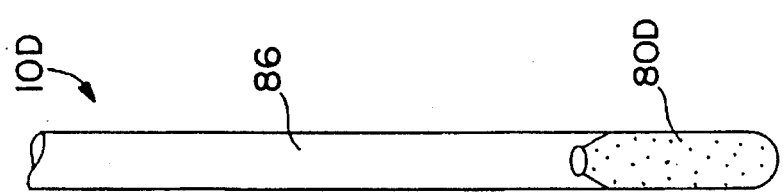
FIG. 3D
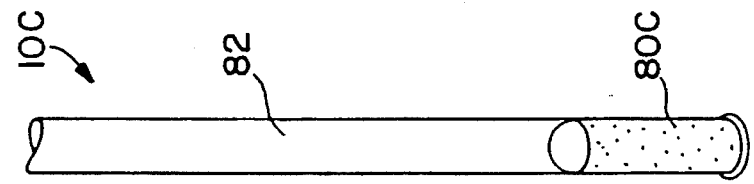
FIG. 3C
FIG. 3B
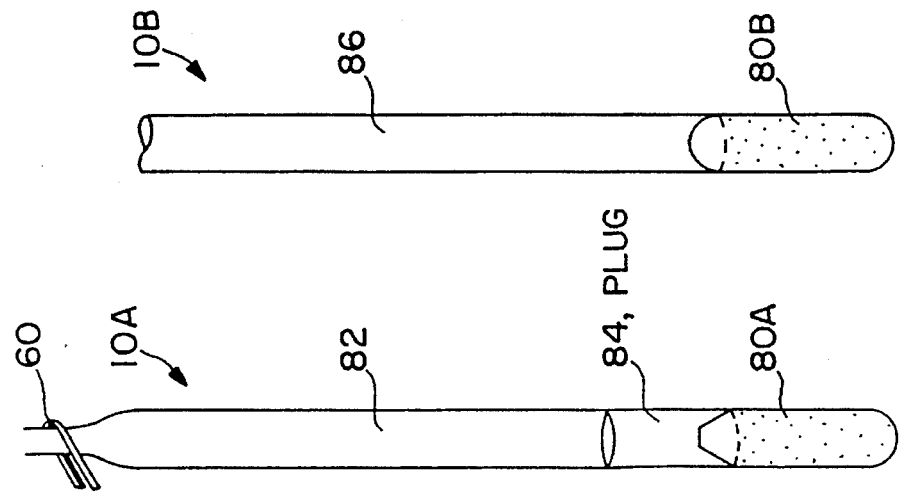
FIG. 3A

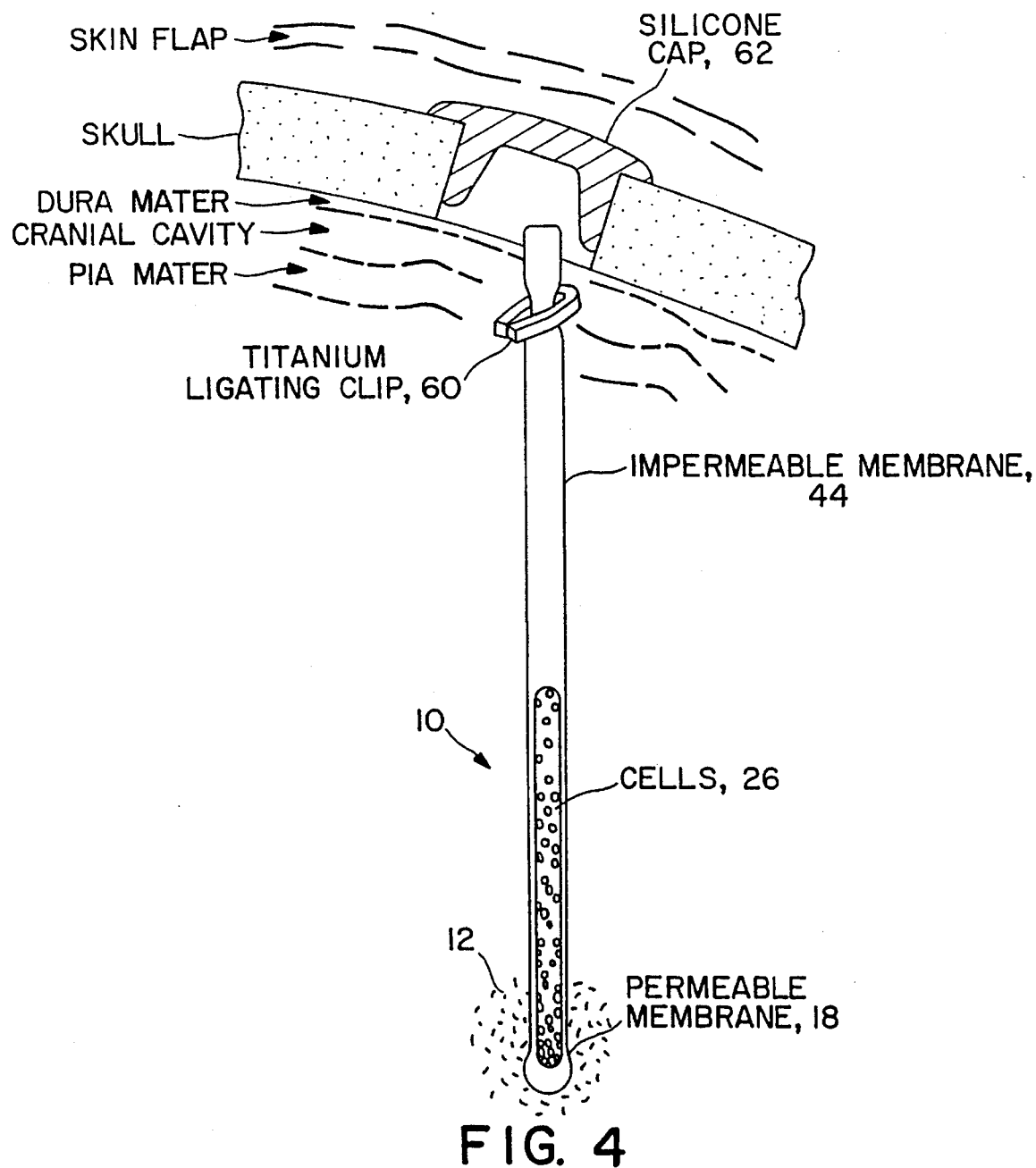

5,487,739

IMPLANTABLE THERAPY SYSTEMS AND METHODS

CROSS-REFERENCE TO RELATED APPLICATION

This is a continuation of application Ser. No. 07/998,368, filed Dec. 30, 1992, entitled IMPLANTABLE THERAPY SYSTEMS AND METHODS now abandoned, which is a continuation-in-part of U.S. patent application Ser. No. 722,947 filed Jun. 28, 1991, entitled "Neural Implant Method and System" now abandoned, which is a continuation-in-part of U.S. patent application Ser. No. 369,296 filed Jun. 21, 1989 now abandoned, entitled "Neurological Therapy Devices", which is a continuation-in-part of U.S. patent application Ser. No. 121,626, filed Nov. 17, 1987, entitled "In vivo Delivery of Neurotransmitters by Implanted, Encapsulated Cells", now U.S. Pat. No. 4,892,538.

BACKGROUND OF THE INVENTION

The technical field of this invention includes the treatment of neurological disorders and treatment of acute and/or chronic pain. In particular, the invention concerns the treatment of diseases and disorders which may be remedied by treatment with secretory substances, such as neurotransmitters, neuromodulators, hormones, trophic factors, or growth factors, as well as the reduction of pain sensitivity by the provision of a sustained local delivery of neuroactive substances, particularly catecholamines and opioid peptides. All these substances are characterized by the fact they are secreted by "source" cells and produce a specific change in the source cell itself or in a "target" cell (i.e., they are biologically active).

Deficits in secretory substances have been implicated in various neurological diseases. Lack of neurotransmitter-mediated synaptic contact causes neuropathological symptoms, and can also lead to the ultimate destruction of the neurons involved.

For example, paralysis agitans, more commonly known as Parkinson's disease, is characterized by a lack of the neurotransmitter, dopamine, within the striatum of the brain, secondary to the destruction of the dopamine secreting cells of the substantia nigra. Affected subjects demonstrate a stooped posture, stiffness and slowness of movement, and rhythmic tremor of limbs, with dementia being often encountered in very advanced stages of the disease.

The direct administration of purified or synthetic dopamine, its precursors, analogs and inhibitors has been studied for therapeutic value in the treatment of Parkinson's disease. These studies have revealed various problems with delivery, stability, dosage, and cytotoxicity of the applied compounds. To date, none of these approaches has demonstrated more than marginal therapeutic value. Brain derived growth factor also may have potential value in the treatment of Parkinson's disease since it has been demonstrated to maintain the viability of striatal neurons in vitro.

Many other diseases, especially neurological disorders appear to be based in whole, or in part, on the absence or limited availability, to target cells or regions, of a critical biological factor.

It is also fairly well established that the activation of noradrenergic or opioid receptors in the spinal cord by direct intrathecal injection of α-adrenergic or opioid agonists produces antinociception, and that the co-administration of subeffective doses of these agents can produce potent analgesia. The presence of enkephalin-secreting neurons and opiate receptors in high densities in the substantia gelatinosa of the spinal cord and the resultant analgesia observed following local injection of opiates into the spinal cord have suggested a role for opioid peptides in modulating the central transmission of nociceptive information. In addition, catecholamines also appear to be important in modulating pain sensitivity in the spinal cord since injection of noradrenergic agonists into the subarachnoidal space of the spinal cord produces analgesia, while the injection of noradrenergic antagonists produces increased sensitivity to noxious stimuli.

In an attempt to provide a continuous supply of drugs or other factors to the brain and other tissues at a controlled rate, miniature osmotic pumps have been used. However, limited solubility and stability of certain drugs, as well as reservoir limitations, have restricted the usefulness of this technology. For example, controlled sustained release of dopamine has been attempted by implanting dopamine encapsulated within bioresorbable microcapsules (McRae-Degueurce et al. (1988) Neurosci. Lett. 92:303–309). However, controlled sustained release of a drug from a bioresorbable polymer may rely, e.g., on bulk or surface erosion, which may be due to various hydrolytic events, increasing the likelihood of drug degradation, and rendering predictable release rates difficult. Others may be limited to finite loading of the polymer, and may lack any cellular feedback regulation.

Many drugs have been administered intraspinally in the clinical setting, and numerous methods are available to deliver intraspinal medications. For instance, the most common method of intraspinal drug delivery, particularly anesthetics, is continuous infusion by way of spinal catheters. However, the use of these catheters, particularly small-bore catheters, has been implicated in such complications as cauda equina syndrome, a neurological syndrome characterized by loss of sensation or mobility of the lower limbs. In fact, the FDA was prompted to issue a safety alert in May, 1992, alerting Anesthesia Care Providers to the serious hazard associated with continuous spinal anesthesia by small-bore catheters and has taken action to remove all small-bore catheters from the market.

The implantation of cells capable of constitutively producing and secreting neuroactive factors has also been attempted. Recently, remedial transplantation of neurotransmitter-secreting tissue has been accomplished using the patient's own tissue so as not to elicit an immune response. For example, dopamine-secreting tissue from the adrenal medulla of patients suffering from Parkinson's disease has been implanted in their striatum with some success. However, this procedure is only used in patients less than 60 years of age, as the adrenal gland of older patients may not contain sufficient dopamine-secreting cells. This restriction limits the usefulness of the procedure as a remedy since the disease most often affects older people. A further problem associated with this procedure is that it requires an additional, distinct surgical procedure.

Other transplantation approaches have demonstrated that even though the Central Nervous System (CNS), e.g. the brain and spinal cord, is considered "immuno-privileged", rejection ultimately occurs with both allografts and xenografts. This problem necessitates the co-administration of immuno-suppressors, the use of which renders their own set of complications and deleterious side-effects. For example, human medullary tissue has been implanted into the subarachnoid space of patients suffering from terminal cancer and has been shown to reduce both acute and chronic pain. However, the limited availability of human donor tissue for allografts reduces the potential for its large scale use, suggesting the need to utilize xenographic donors. It is clear that the use of widely disparate histoincompatible species (i.e. bovine and human) can result in severe immunological responses, which can cause the ultimate destruction of the graft. The immunosuppresent cyclosporine A has been used to prolong bovine adrenal medullary chromaffin cell xenografts in the rat CNS, but survival is variable and cyclosporine A can be toxic with potentially serious complications including hepatotoxicity and nephrotoxicity, as well as tumorogenicity. With regard to the use of cyclosporine A in humans, the serious side effects associated with its use have precluded its administration to otherwise healthy patients.

A number of researchers have proposed the use of microcapsules, i.e., tiny spheres which encapsulate a microscopic droplet of a cell solution, for both therapeutic implantation purposes and large scale production of biological products. However, there are a number of shortcomings to the microencapsulation approach. For example, the microcapsules can be extremely difficult to handle, including being difficult to retrieve after implantation. The types of encapsulating materials which can be used are constrained by the formation process to polymers which can dissolve in biocompatible solvents. Furthermore, due to the limited diffusional surface area per unit volume of larger size spheres, only a limited amount of tissue can be loaded into a single microcapsule.

An alternative approach has been macroencapsulation, which typically involves loading cells into hollow fibers and then sealing the extremities. In contrast to microcapsules, macrocapsules offer the advantage of easy retrievability, an important feature in therapeutic implants, especially neural implants. However, the construction of macrocapsules in the past has often been tedious and labor intensive. Moreover, due to unreliable closure, conventional methods of macroencapsulation have provided inconsistent results.

Therefore, there exists a need for improved therapies for the treatment of neurological and other disorders in general, and in particular, a need for therapy devices which can augment or replace the functions of dysfunctional areas of the brain or other organs without causing excessive trauma. There also exists a need for improved therapy to alleviate pain, particularly in the form of sustained analgesic delivery systems. More specifically, there exists a need for a method of providing active, neuroactive factor to a localized region of the nervous system of a subject, the correct dosage of which will be constitutively delivered over time.

Accordingly, it is an object of the present invention to provide an implantable, retrievable therapy device useful for the sustained and controlled delivery of a biologically active factor to a subject, and more particularly, to provide a device which can deliver a biologically active factor, e.g., a neuroactive factor or growth factor, to a localized region in the CNS of a subject.

SUMMARY OF THE INVENTION

Neurological therapy methods and systems are disclosed for the local and controlled delivery of a biologically active factor to the brain, or other portion of the CNS, or other organ of a subject. The methods and systems are useful for treating subjects suffering from a deficiency or organ dysfunction, or suffering from acute and/or chronic pain.

A method of the invention involves surgically exposing an insertion site generally located above a predetermined treatment site, which site may be within brain tissue or other target organ tissue. The precise location of the treatment site, and the subsequent insertion site location may be stereotaxically ascertained. A cannula, having an obturator positioned therein, is inserted at the insertion site, defining a passageway to the treatment site. The cannula generally has an open proximal end for receiving the obturator, and an open distal end for delivery of biologically active factors to the treatment site.

The method further involves removing the obturator from the cannula once the passageway is defined and the cannula is in the desired position. After the obturator is removed, a biocompatible vehicle containing a biologically active factor is inserted into the cannula along the passageway. Once the vehicle is positioned near the distal end of the cannula, the cannula is removed from the passageway, leaving the vehicle positioned at the treatment site.

The obturator may be re-inserted into the cannula after the vehicle is initially placed in the cannula to position the vehicle at the distal end. This may be necessary if, for example, the vehicle does not slidably fit within the cannula. The obturator used for thus positioning the vehicle may be the same as or different from the obturator initially positioned in the cannula. If an obturator is used to position the vehicle, it is removed following removal of the cannula to further assist in retaining the desired position of the vehicle at the treatment site.

Another form of the invention involves making an insertion site proximal to the treatment site, and introducing a guidance needle, optionally with an obturator positioned in its central bore, into the area of the treatment site. The needle lumen is opened by removing the obturator if any is present, and a guidewire is introduced into the lumen of the needle and is fed through until it enters the treatment site. Once the guidewire is contacting the treatment site, the guidance needle is removed and replaced with a cannula. The cannula is ideally dimensioned for providing an insertion path for positioning a biocompatible vehicle containing biologically active factors at the desired treatment site. The guidewire is removed, and the vehicle is inserted into the cannula and guided along the passageway of the cannula towards the treatment site. Once the vehicle is positioned near the distal end of the cannula (i.e. at the treatment site), the cannula is removed from the passageway, leaving the vehicle at the treatment site.

A pusher can be inserted into the cannula after the vehicle is initially placed in the cannula so as to aid in positioning the vehicle at the distal end. As above, this may be necessary if, for example, the vehicle does not slide freely within the lumen of the cannula.

In another form of the invention, the insertion site is enlarged by introducing at least one dilator over the guidewire before the insertion of the cannula.

In another form of the invention, the cannula is filled with a physiologically compatible solution following removal of an obturator or a dilator and prior to inserting the vehicle. In this manner, the fluid serves as a lubricant to assist in positioning the vehicle at the distal end of the cannula.

The vehicles used in practicing the method of the invention, include capsules containing biologically active factors. These capsules may include an integral tether that extends from the capsule. The tether preferably is of a length sufficient to reach at least from the treatment site to the proximity of the insertion site. The tether may also be a part of the cell capsule itself that extends above the insertion site. In addition, the tether may form a secondary seal on the capsule. Once the vehicle capsule is positioned in the passageway to the treatment site, the tether may then be secured at the insertion site, e.g., by securing the tether to the outer surface of the skull proximal to the insertion site by means of surgical staples, biocompatible adhesive, and the other methods available and known to those skilled in the art. Following positioning of the vehicle at the treatment site, the insertion site may be closed or capped to prevent introduction of extraneous material to the passageway and the treatment site.

In one aspect of the invention, the vehicle may include an amount of a detectable marker, such as a radio-opaque material, to facilitate in situ monitoring of the vehicle at the treatment site. The vehicle may then post-operatively be monitored in the patient through the use of CAT scan, MRI or the like.

Systems for providing encapsulated biological material to a selected treatment site are also disclosed. A system that can be used to practice the method of the invention includes a cannula, an obturator, and a biological vehicle. The cannula is adapted to receive the vehicle, having an open proximal end for receiving the obturator and the vehicle, and an open distal end for delivering the vehicle to the treatment site. The obturator is of the type designed for insertion within and along a substantial length of the cannula to prevent backfill of materials, such as dura, into the cannula during insertion of the cannula to the treatment site. The obturator is also adapted to assist in positioning the encapsulated neuroactive factors within the cannula.

Another system that can be used to practice the method of the invention includes a guidance needle, a guidewire, a cannula, and a biological vehicle. The guidance needle has a lumen adapted to receive the guidewire, such that the guidewire can be fed therethrough from an open proximal end adapted for receiving the guidewire to an open distal end which can be placed at or proximate the treatment site. The guidance needle is removable from the insertion site and disconnectable from the guidewire without affecting the guidewires ultimate position at the desired treatment site. The cannula has a bore adapted for receiving the vehicle and the guidewire, having an open proximal end for receiving the vehicle, and an open distal end for delivering the vehicle to the treatment site. The system can further include an obturator for reversibly blocking the lumen of the guidance needle, as well as dilators adapted for receiving the guidewire and slidable therealong. A pusher can also be used with the system, the pusher adapted for passing through the lumen of the cannula and pushing the vehicle to the distal end of the cannula.

The vehicles of the system of the invention can include a cell capsule having a biocompatible permselective outer membrane encapsulating cells capable of releasing active factors. The vehicle generally has a shape which enables insertion within and movement along the cannula. In one form, the vehicles are smooth, seamless capsules formed by extrusion through a multilumen spinneret. In that form, the capsules are formed from a biocompatible, permselective thermoplastic, encapsulating a suspension of cells that secrete a biologically active factor. Exemplary classes of active factors include neurotransmitters, neuropeptides including opioid peptides, growth factors, trophic factors, and analgesic factors such as catecholamines. In another form, the vehicles are hollow fibers filled with the factor-secreting cells.

The vehicles of the present system further include a tether extending from the capsule for securing the vehicle at the treatment site following insertion. The tether may be integral with the capsule, or may be attached by methods available and known to those skilled in the art.

The term "biologically active factors" used herein includes: neurotransmitters such as gamma aminobutyric acid, serotonin, acetylcholine, , glutamic acid and dopamine; and neuroactive analgesic factors such as catecholamines (e.g. epinephrine and norepinephrine) and opioid peptides. The term also includes precursors, agonists, active analogs, and active fragments of these neurotransmitters (e.g. dopamine precursor L-dopa and dopamine agonist bromocriptine). Cells that secrete neuroactive factors such as peptide neurotransmitters, growth factors, trophic factors, catecholamines, opioid peptides, and/or hormones may also be useful. These include: insulin, Factor VIII, trophic factors such as erythropoeitin and growth hormones, biological response modifiers such as lymphokines and cytokines, enzymes, and antibodies from antibody-secreting cells, neuropeptides such as enkephalins, dynorphins, Substance P, Met-enkephalin, neuropeptide Y, vasoactive intestinal polypeptide, neurotensin, somatostania, and endorphins, catecholamines such as epinephrine and norepinephrine, as well as factors such as nerve growth factor (NGF), brain-derived neurotophic factor (BDNF), neurotrophin-3 (NT-3), an array of fibroblast growth factors, and an array of neurotrophic factors.

The term "semipermeable" is used herein to describe biocompatible membranes that allow the diffusion therethrough of molecules having a relatively low molecular weight, i.e., approximately 150 kD, while excluding the passage of those having a relatively high molecular weight.

In one embodiment of the invention, the semipermeable membrane of the receptacle preferably contains pores having a molecular weight exclusion of about 150 kD. This membrane excludes the passage therethrough of large particles such as those which are capable of degrading the neurotransmitter or injuring the neurotransmitter-producing cells (e.g. viruses, antibodies, complement, and various proteases). The semipermeable membrane can be made of various polymeric compositions such as a polyvinylchloride, polyacrylonitrile, polyvinylidene fluoride, polystyrene, polyurethane, polyamides, cellulose acetates and nitrates, polymethylmethacrylate, polysulfones, polyacrylates including acrylic copolymers, and derivatives, copolymers, and mixtures thereof.

The encapsulated cells may include secretory cells which have been isolated from natural sources, or have been genetically engineered to produce neuroactive factors, growth factors or agonists, precursors, active analogs, or active fragments thereof. For example, chromaffin cells of the adrenal medulla, embryonic ventral mesencephalic tissue, and various neuroblastic cell lines such as PC12 function to supply dopamine and other active factors, and therefore, are preferred for incorporation into the device. In some aspects of the invention, the cell is an allograft (i.e., cells from another of the same species as the subject in which it is to be implanted) or a xenograft (i.e., cells from another of a different species).

The invention will next be described in connection with certain illustrated embodiments. However, it should be clear that various modifications, additions, and subtractions can be made without departing from the spirit or scope of the invention. For example, the present invention should not be read to require, or be limited to, a particular device shape, material, neuroactive factors, growth factor, or cell line described by way of example or illustration.

BRIEF DESCRIPTION OF THE DRAWINGS

The invention itself can be more fully understood from the following description when read together with the accompanying drawings in which:

FIGS. 1A–1G are a series of schematic drawings illustrating the steps of an exemplary method of implanting a biological vehicle;

FIGS. 2A–2J are a series of schematic drawings illustrating the steps of another exemplary method of implanting a biological vehicle;

FIGS. 3A, 3B, 3C, 3D and 3E show various alternative designs for implantable neurological therapy devices; and FIG. 4 is a schematic illustration of an implantable neurological therapy device according to the system of the present invention.

Like reference characters in the respective figures indicate corresponding parts.

DETAILED DESCRIPTION

Figure 1C:
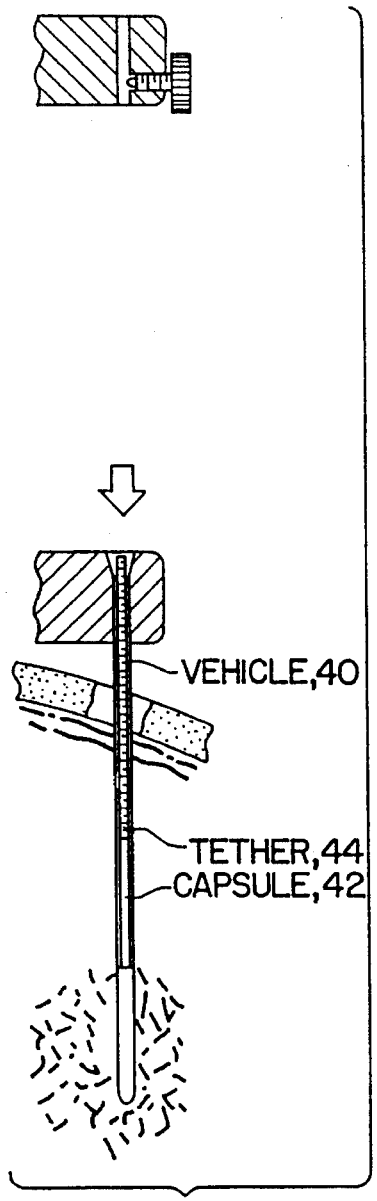

The invention disclosed herein concerns methods and systems for the constitutive and controlled delivery of biologically active factors, such as neurotransmitters, neuroactive factors, fibroblast growth factors and the like, as well as precursors, agonists, active fragments, and active analogs thereof, to a target treatment site within a patient.

FIGS. 1A–1G illustrate the steps involved in practicing an exemplary method of the present invention. Generally, the method involves surgically exposing an insertion site 10 located above a desired, pre-determined treatment site 12. A cannula 20 is fitted with an obturator 30, and the cannula/obturator assembly 25 is inserted at insertion site 10. The obturator 30 is then removed from within the cannula 20, and a biocompatible vehicle (40 in FIG. 1C) is inserted into the cannula 20. Once the vehicle 40 is appropriately positioned, the cannula 20 is removed, leaving the vehicle 40 in position at the treatment site 12.

Specifically, FIG. 1A illustrates the cannula 20, having an inserted obturator 30, positioned through the insertion site 10 to the target treatment site 12. The obturator 30 preferably is a blunt-end obturator to minimize or prevent tissue damage. This positioning of the cannula 20 forms a passageway to the treatment site 12. The specific location of the insertion site is determined using a stereotaxic assembly including a cannula mount 14 and an obturator mount 16. The mounts 14, 16 are used to sterotaxically position the cannula 20 for accurate placement at the treatment site 12. In a preferred embodiment, an isodiametric stereotaxic apparatus is used that is commercially available from Radionics, Burlington, Mass.

The cannula 20 may be of any commercially available type. Generally, it has an open proximal end 20a for insertion of the obturator 30 and the encapsulation cell vehicle 40. The cannula 20 also has an open distal end 20b for delivering the vehicle 40 to the treatment site. In addition, the cannula 20 includes a central bore 26, with a substantially smooth interior surface. The distal end 20b may be blunt, rounded, or pointed, depending on the tissue structure into which it will penetrate, the acceptable amount of ancillary damage, and other such considerations.

In one embodiment, the cannula 20 can be constructed of polytetrafluoroethylene (Teflon™) or similar low friction polymers to minimize the risk of abrasive damage to the vehicles during insertion. Specifically, a Teflon™ barrel featuring a gradual reduction of both the inside and outside diameters and a thinning of the cannula wall of the tip can be employed. Such low friction polymeric cannulae are more easily inserted into and removed from the brain (or other target site) and can be made to be transparent to permit monitoring of the progress of the vehicle through the cannula, and verification that there is no blood or debris in the cannula that could affect the vehicle's biocompatibility.

Polymers such as polytetrafluoroethylene not only minimize friction but also assure that the encapsulated cell vehicle's surface is not contaminated with metals or metal ions as it passes through the cannula. Finally, the "tapering" feature at the end of cannula 20 (caused by the reduced thickness of the distal end 20b) serves to verify obturator/pusher clearance from the end of the cannula to eliminate the possibility of over, or under, driving the vehicle during insertion.

As shown in FIG. 1A, the cannula 20 is positioned at the treatment site 12 with the obturator 30 inserted therein to prevent material, such as dura and the like, from entering the cannula 20 during insertion. Alternate methods and devices may be used to achieve similar results.

The next step, illustrated in FIG. 1B, involves removing the obturator 30 from within the cannula 20. This may be achieved either by using the obturator mount 16, or manually. The cannula 20 remains at the treatment site 12, and is generally free of extraneous material along its central bore 26.

The next step, illustrated at FIG. 1C, involves placing a cell encapsulation vehicle 40 at the treatment site 12. The vehicle 40 is generally of a predetermined shape to slidably fit within the central bore 26 of the cannula. In a preferred embodiment, the vehicle 40 is a tethered capsule containing biologically active factors. In that embodiment, the vehicle 40 includes a capsule 42 containing the biologically active factor, with a tether 44, or rod, extending therefrom. The tether 44 is of a length sufficient to reach from the capsule 42, at the treatment site 12, to a location external to the insertion site 10, and may be an extension of the cell vehicle.

In one form of the inventive method, prior to inserting the vehicle 40, the central bore 26 of the cannula is filled with a physiologically compatible solution, such as sterile saline. The vehicle 40 is then inserted within the cannula, and the solution acts as a lubricant to assure passage of the vehicle to the distal end 20b of the cannula.

Figure 1D:
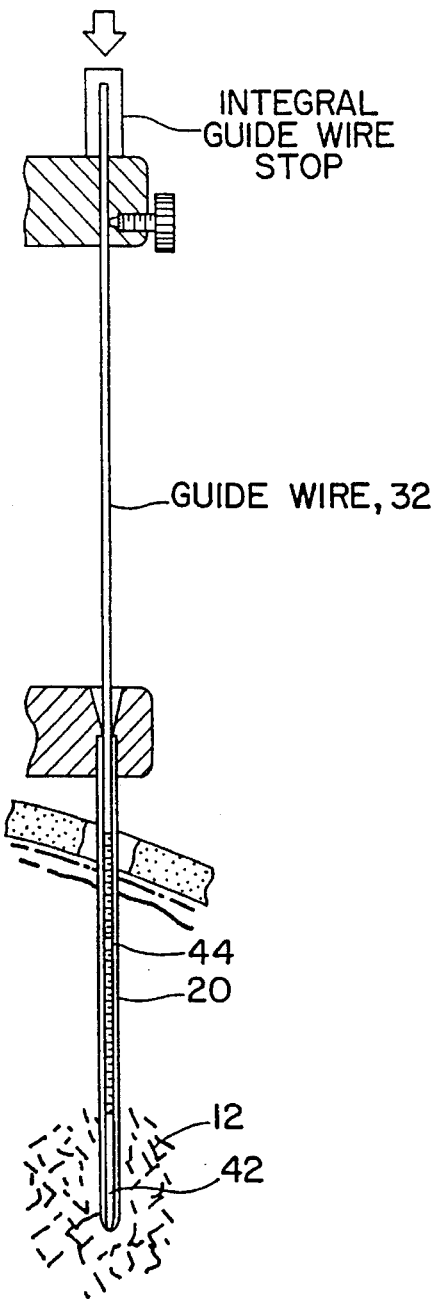

Alternatively, and as illustrated in FIG. 1D, following insertion of the vehicle 40 within the cannula 20, a guide wire 32 may be inserted to assist in positioning the vehicle 40 at the distal end 24 of the cannula. The guide wire 32 may be either the same obturator 30 as that initially positioned within the cannula, a different obturator, a guide wire, or the like. The guide wire 32 is placed above the vehicle 40 within the cannula, and the vehicle 40 is gently pushed into position at the distal end 24 of the cannula.

Figure 1E:
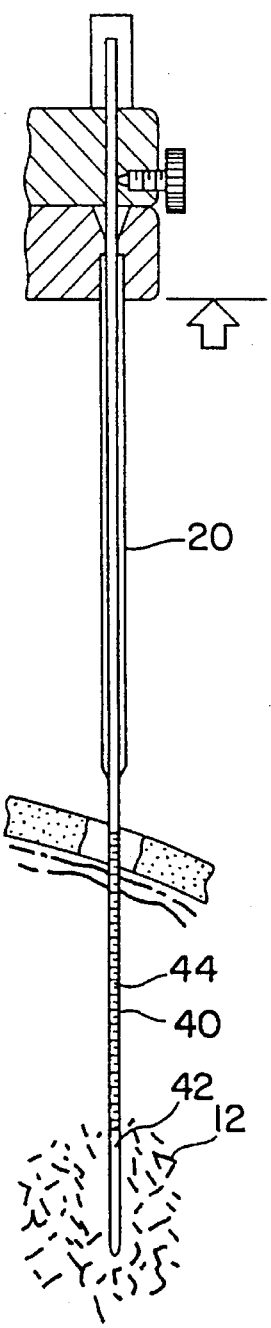

Finally, the cannula 20 is removed from the treatment site 12, as illustrated in FIG. 1E. If a guide wire 32 or other device is used in the preceding step to position the vehicle 40, generally that device 32 is removed following the cannula 20. As with the obturator 30, the cannula 20 may be removed either by the cannula mount 14 or manually. The end result is positioning of the vehicle 40 at the treatment site 12.

Figure 1F:
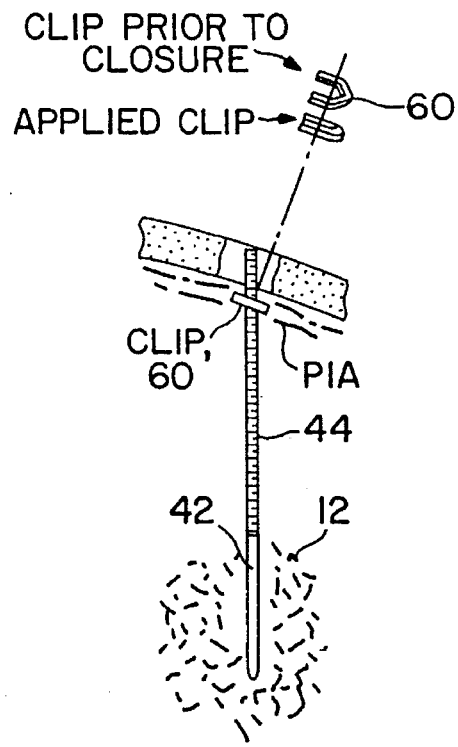
Figure 1G:
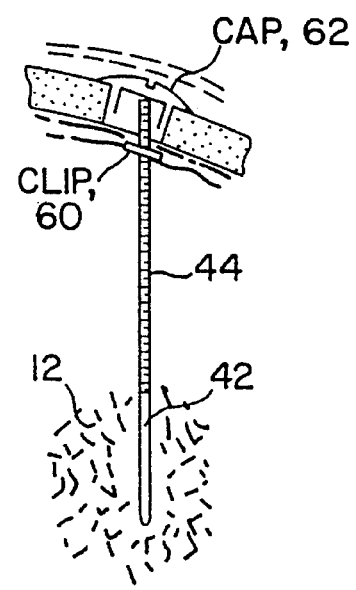

If the vehicle 40 is a tethered capsule, the tether 44 may be secured adjacent the insertion site 10 by means of a surgical clip 60 or the like, shown in FIG. 1F. In that, preferred form of the inventive method, the tether 44 allows the vehicle 40 to be retrieved from the treatment site 12. As a final, optional step, a cap 62 may be used to seal the insertion site 10 to prevent introduction of extraneous material through the insertion site (FIG. 1G).

The method described above is well suited for implantation of encapsulated cells into the brain, but may be used to introduce biologically active factors to other structures and organs. In practicing the inventive method, multiple vehicles may be required on each side of the patient's brain. Each vehicle is inserted in the same fashion, as described above. An initial scan, such as a CAT scan, may be performed on the patient to determine the precise location of the treatment site. For example, in treating Parkinson's disease, the basal ganglia, specifically the substantia nigra, is identified as the treatment site.

FIGS. 2A–2J illustrate the steps involved in practicing another exemplary method of the present invention, which is particularly well suited for intraspinal implantation of encapsulated cells, especially intrathecal implantation of encapsulated cells within the subarachnoid space of the spinal column, or other treatment sites where initial entry is better gained by the use of a needle or cannula of smaller diameter than ultimately needed to introduce the biological vehicle. Generally, the method involves surgically exposing an insertion site 10' located above a desired, predetermined treatment site 12'. Where the predetermined treatment site 12' is the subarachnoid space (116 in FIG. 2J), an incision can be made over the interspace of two vertebrae 110, such as between the L-3 and L-4 vertebrae, in a manner similar to the preparation needed for administration of a lumbar anesthetic. A guidance needle 100 is introduced into the insertion site and the distal end 100B of the guidance needle 100 is located at or proximate to the treatment site 12'. A guidewire 102 is inserted down the lumen 101 of guidance needle 100 such that the distal tip 103B of guidewire 102 is also located at or proximate the treatment site 12'. The guidewire 102 and guidance needle 100 are so dimensioned that the guidance needle 100 can be withdrawn from the treatment site 12' without significantly altering the position of the distal end 103B of guidewire 102 relative to the treatment site 12'. Further, the proximal end 103B of guidewire 102 is dimensioned so that guidance needle 100 can be withdrawn free of guidewire 102. A cannula 20 can then be directed along guidewire 102 such that its distal end 20B is positioned at the treatment site 12'. The guidewire 102 is then withdrawn from the central bore 26 of cannula 20, and a cell capsule vehicle 40 is inserted into the cannula 20. Once the vehicle 40 is appropriately positioned, the cannula 20 is removed, leaving the vehicle 40 in position at treatment site 12'. Where desired, a dilator 104 can be introduced along the guidewire prior to or concomitant with the insertion of the cannula. The dilator 104 can be used separately to expand the insertion site, as well as used with the cannula 20 to act as an obturator and improve the guidance of the cannula 20 along the guidewire 102.

Figure 2A:
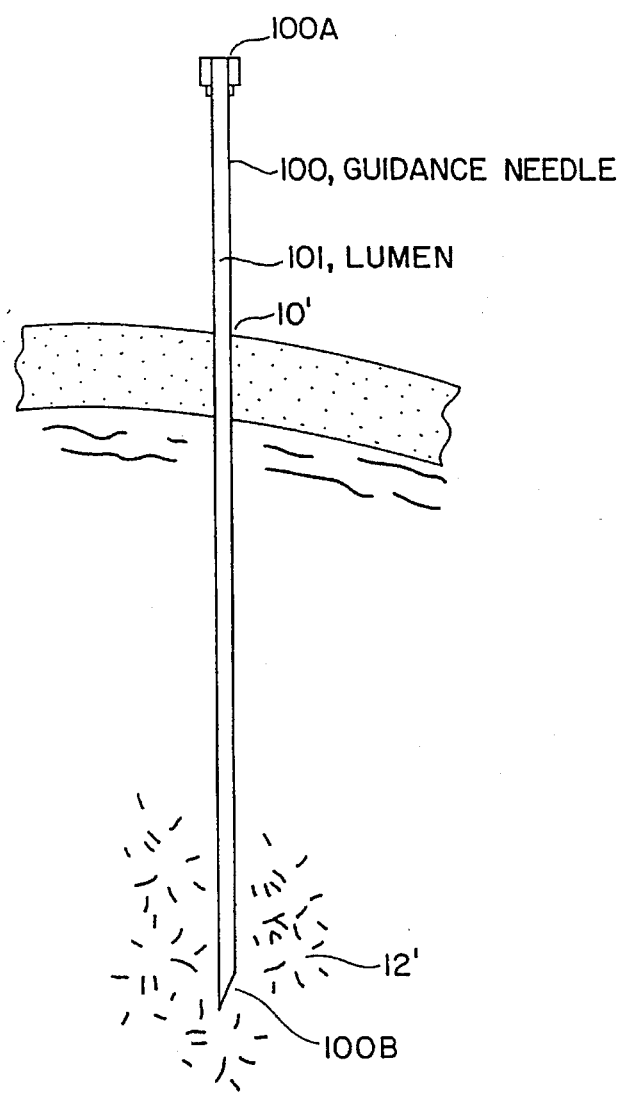

Specifically, FIG. 2A illustrates the guidance needle 100 positioned through an insertion site 10' so that its distal tip 100B is located at or proximate the target treatment site 12'. If desired, the guidance needle 100 can also include a removable obturator (not shown) positioned in its lumen 101. As illustrated in FIG. 2J, in the instance where the treatment site 12' is in the subarachnoidal space 116, the guidance needle 100 can be a Tuohy needle or similar needle thereto. By way of illustration, the Tuohy needle is introduced between the L-3 and L-4 vertebrae 110 with the open side of the needle facing the head (i.e., curved portion of the needle caudal) at a 30°–40° angle, through the ligamentum flavum 112 and epidura 114 and into the subarachnoid space 116. If desired, a sample of fluid can be removed through the guidance needle and tested for the presence of cerebral spinal fluid (CSF), using assays such as the determination of glucose levels in the fluid (e.g. a glucose level near 100 mg/dL is indicative of CSF).

Figure 2B:
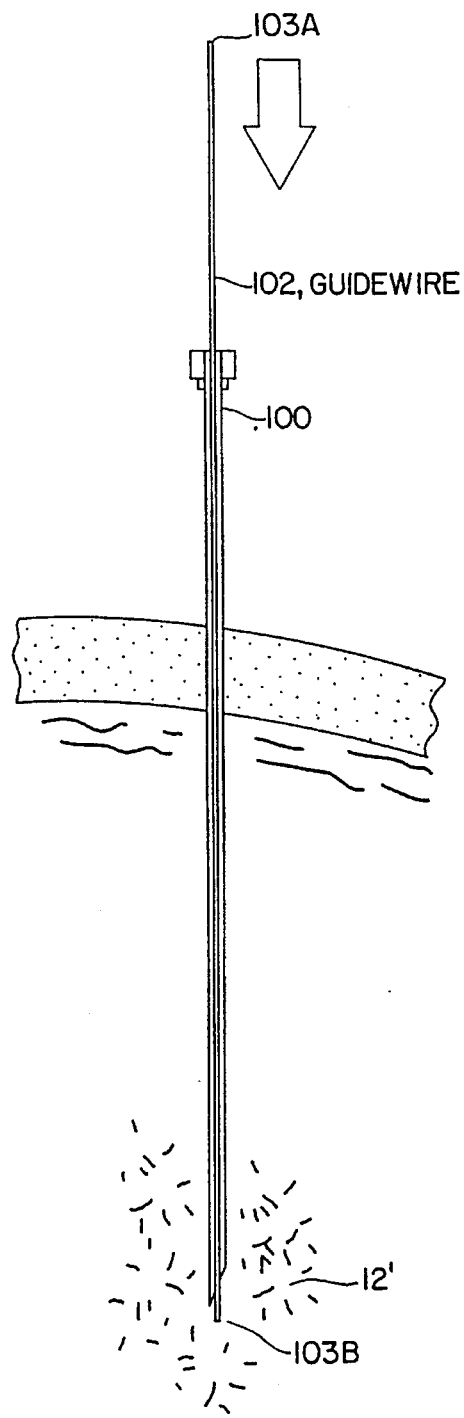

As illustrated by FIG. 2B, once the guidance needle 100 is located at the treatment site 12', a guidewire 102 is fed through the lumen 101 of the needle 100 so that the distal end 103B of guidewire 102 is also located at or proximate to the treatment site 12'. If the needle 100 has an obturator, the obturator is removed to provide an open lumen 101 for passage of guidewire 102. The guidewire 102 is so dimensioned that it can pass through the lumen 101 of needle 100, from the needle's proximal end 100A to its distal end 100B, such that, as shown in FIG. 2C, needle 100 can be removed entirely from the treatment site 12', leaving the guidewire 102 in place and free of needle 100.

If desired, the insertion site can be enlarged by introducing at least one dilator 104 over the guidewire 102. As illustrated by FIG. 2D, dilator 104 is introduced through the insertion site and towards the treatment site 12' by tracking the path of guidewire 102, with the guidewire passing through the bore 105 of dilator 104. Dilator 104 can be used to increase the size of the insertion site to ultimately accommodate a cannula of a given size. The dilator 104 is especially useful for spreading apart tissue including muscle and cartilage as well as spreading closely spaced bone, such as found when trying to penetrate to the subarachnoid space of the spinal column.

As illustrated in FIG. 2E, the cannula 20, having the final dilator 104 housed within its central bore 26, can then be introduced over the guidewire, and its distal end 20B positioned at the treatment site 12' for the introduction of the biological vehicle 40. Having a dilator disposed within the cannula 20 serves a number of useful purposes including keeping the bore 26 of cannula 20 substantially free from tissue (e.g. dural matter) upon insertion, as well as providing better guidance by virtue of the guidewire 102 being passed through the smaller diameter bore 105 of dilator 104 rather than the larger bore 26 of cannula 20. However, it is clear that any intermediate steps of disposing dilators along guidewire 102 are not required, and that, if desired, the cannula 20 can be disposed directly along the guidewire 102 without use of any dilators. The cannula 20 illustrated in FIGS. 2A–2I is substantially identical to that illustrated in FIGS. 1A–1G, but need not be adapted for use with a stereotactic frame. Additionally, where the insertion path is not a straight line, the cannula may be curved similarly to the guidance needle.

The next step, illustrated in FIG. 2F, is to remove the guidewire and any dilator that may be disposed in the bore 26 of cannula 20. Thus, the distal end 20B of cannula 20 remains at the treatment site 12, and is generally free of extraneous material along its central bore 26.

Figure 2G:
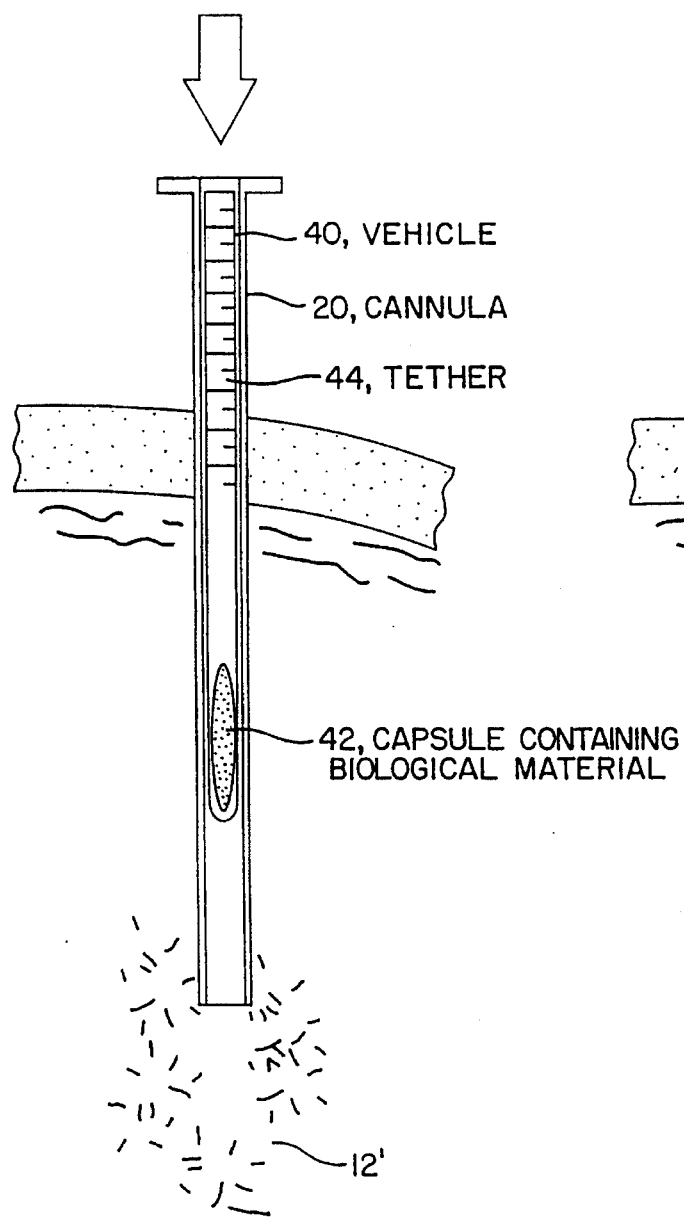

The next step, illustrated at FIG. 2G, involves placing a cell encapsulation vehicle 40 at the treatment site 12'. Similar to the method illustrated in FIGS. 1A–1G, the vehicle 40 is generally of a predetermined shape to slidably fit within the central bore 26 of the cannula 20. In a preferred embodiment, the vehicle 40 is a tethered capsule containing biologically active factors. In that embodiment, the vehicle 40 includes a capsule 42 containing the biologically active factor, with a tether 44, or rod, extending therefrom. The tether 44 is of a length sufficient to reach from the capsule 42, at the treatment site 12', to a location external to the insertion site 10', and may be an extension of the cell vehicle.

In one form of the inventive method, prior to inserting the vehicle 40, the central bore 26 of the cannula 20 is filled with a physiologically compatible solution, such as sterile saline. The vehicle 40 is then inserted within the cannula, and the solution acts as a lubricant to assure passage of the vehicle to the distal end 20B of the cannula.

Figure 2H:
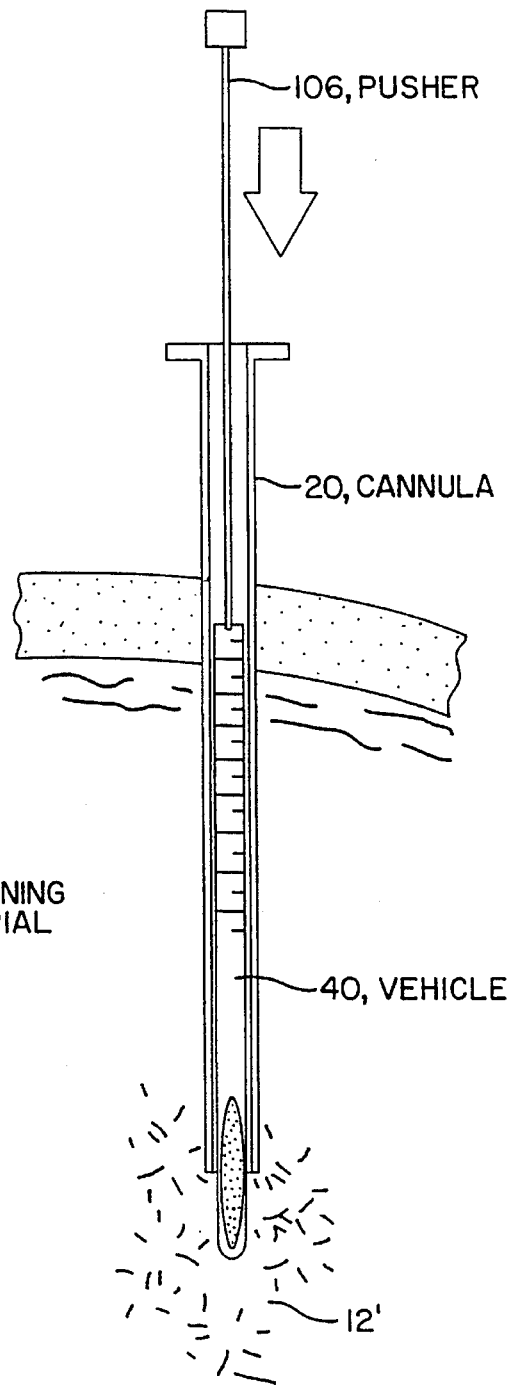

Alternatively, and as illustrated in FIG. 2H, following insertion of the vehicle 40 within the cannula 20, a pusher 106 may be inserted to assist in positioning the vehicle 40 at the distal end 20B of the cannula. The pusher 106 may be either an obturator dimensioned for the cannula 20, a guide wire, or the like. The pusher 106 is placed above the vehicle 40 within the cannula, and the vehicle 40 is gently pushed into position at the distal end 20B of the cannula 20.

Figure 2I:
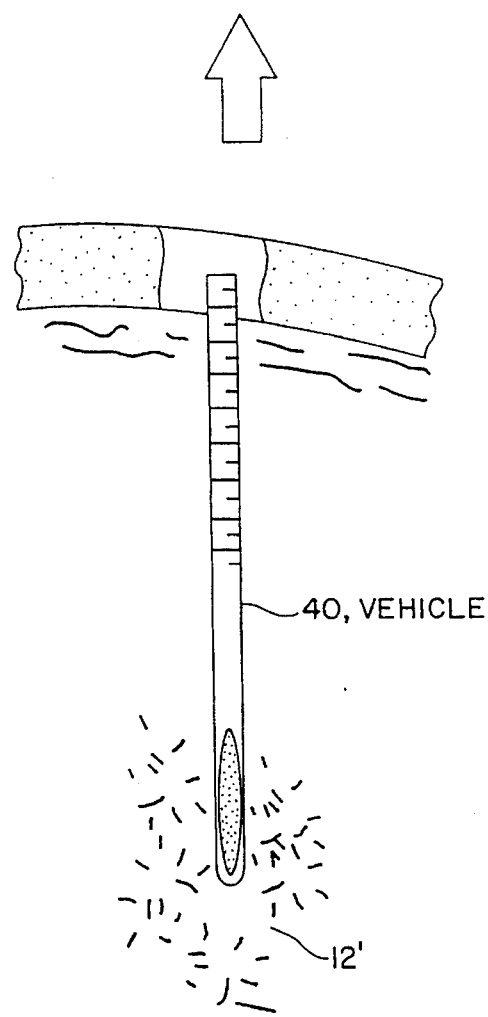
Figure 2J:
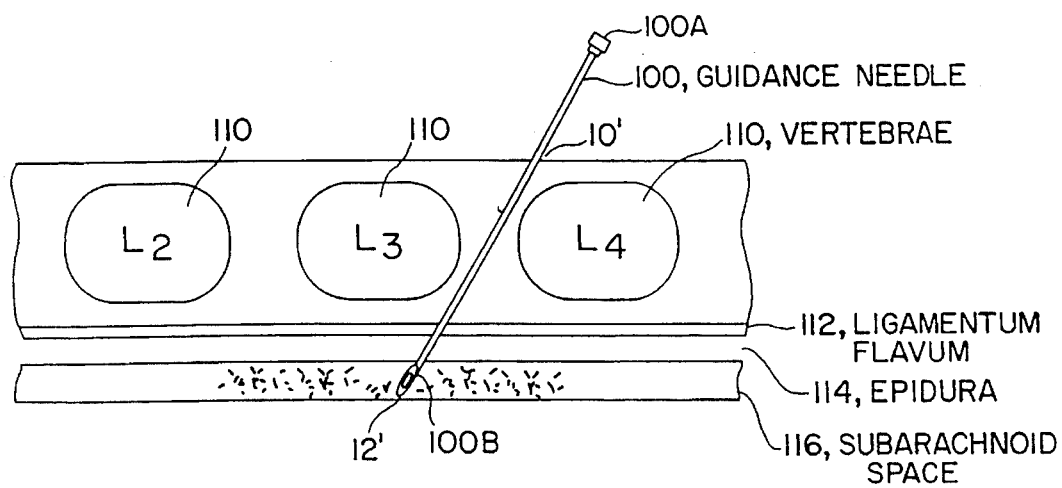

Finally, the cannula 20 is removed from the treatment site 12', as illustrated in FIG. 2I. If a pusher 106 or other device is used in the preceding step to position the vehicle 40, generally that device is removed following the cannula 20 to ensure that the vehicle 40 remains at treatment site 12' and is not accidentally moved with the withdrawal of the cannula 20.

In one particular embodiment, the system of this invention comprises: an 18 gauge, 4 inch long Tuohy needle with styler and hub (Popper & Sons); a 0.032 inch×31 inch flexible guide wire (Lake region, Act modified); a 7-French vessel dilator (#392306, Argon Medical); a 6-French 30cm dilator and TEFLON sheath with stopcock removed (Angestat HG06-0, Angeion) where the sheath corresponds to the cannula 20 and the 6F dilator corresponds to the dilator 104 in FIG. 2E; a pusher having a 0.054"×187 mm wire pusher (with a 255 mm handle); and a biological vehicle comprising bovine or porcine adrenal chromaffin cells suspended in an alginate matrix and encapsulated in a PAN/PVC capsule (750 μm ID×950 μm OD×5 cm; 25μl volume) with a 195 mm occluded lumen silicone tether (Speciality Silicone Fabricators).

In FIGS. 1A–1G and 2A–2I, the vehicle 40 has the shape of a rod. However, it should be appreciated that the vehicle 40 may have any shape which can accommodate the source of biologically active factor, or cells which release active factors, without causing undue trauma to the patient during implantation. The present immunoisolatory vehicle can be formed in a wide variety of shapes and combinations of suitable materials. A primary consideration in selecting a particular configuration for the vehicle when cells are present is the access of oxygen and nutrients to the isolated cells or tissues, and passage of waste metabolites, toxins and the secreted product from the vehicle. The instant vehicle must provide, in at least one dimension, sufficiently close proximity of any isolated cells in the core to the surrounding tissues of the recipient, including the recipient's bloodstream, in order to maintain the viability and function of the isolated cells. In general, the vehicle will have a maximum depth-to-surface distance of no more than 2 mm in at least one dimension, with a maximum depth of 500 microns being preferred. One or several vehicles may be required to produce the desired effect in the recipient.

In FIGS. 3A through 3E, several alternative embodiments of implantable immunoisolatory vehicles are shown. In FIG. 3A, polymeric capsule 80A (which can have an open end) containing active factor secreting cells is joined to hollow tether 82. The distal end of the hollow tether 82 in FIG. 3A can be plugged, e.g., filled with a plug 84 or chitosan or the like, and the proximal end can be closed by sealing clip 60. In FIG. 3B a closed polymeric capsule 80B similarly containing active factor secreting cells can be simply sealed to a solid tether 86. In FIG. 3C, a cell capsule 80C having polyurethane sealed ends is joined to another hollow fiber 82. In FIG. 3D, a cell capsule 80D having one end that is integrally sealed and the other end plugged (e.g. with polyurethane) is joined to a solid tether 86. Finally, in FIG. 3E, yet another embodiment is shown comprising an open cell capsule 80E sealed with polyurethane 88 at its distal end and joined to a hollow tether 82 at its other (proximal) end. The hollow tether 82 uses a hyaluronic acid plug 90 to hold the cells in place and is sealed at its proximal end by clip 60.

It should be clear that various other alternative vehicles can be constructed. The cell capsules can be integrally sealed or plugged with various materials. Likewise, the tethers can be solid or hollow and can be joined to the cell capsules by glues, friction fitting, fusion or the like. The important factor is to construct a device that positions the cell capsules at a predetermined treatment site with sufficient structural integrity to achieve such placement as well as removal intact, if desired at a later date.

In one preferred embodiment, the implantable immunoisolatory vehicle of the present invention is of a sufficient size and durability for complete retrieval after implantation. To be contrasted with such microcapsules, which have a typical maximum practical volume on the order of 1 μl, the preferred immunoisolatory vehicle of the present invention is termed "macrocapsule". Such macrocapsules have a core of a preferable minimum volume of about 1 to 10 μl and depending upon use are easily fabricated to have a value in excess of 100 μl. To increase the therapeutic value provided by tissue encapsulated in microspheres, the number of microspheres must be increased to such a large extent that significant retrievability becomes impossible. Additionally, an increase in the volume of tissue placed within a microsphere requires a corresponding increase in surface area. Within a sphere, because surface area scales with $r^2$ where as volume scales with $r^3$, as the volume of encapsulated tissue volume increases, the required capsule size to provide sufficient surface area for nutrient diffusion quickly becomes impractical. Macrocapsules in the shapes of cylinders or flat sheets do not have these limitations because volume increases more proportionately to surface area such that the diffusional transport of nutrients and products for increased mounts of tissue can be accommodated by increasing the surface area without unwieldy increases in total vehicle size.

The encapsulated cell vehicle 40, shown in further detail in FIG. 4, includes capsule 42 filled with a secretory cell, preferably a cell that produces biologically active factors. In a preferred embodiment, the capsule 42 includes a tether 44 or rod extending from and integral with the capsule. The vehicle further includes a permeable, semi-permeable, or permselective membrane surrounding the capsule 42. The tether 44 is generally constructed from an impermeable membrane material or may be coated with a material which makes the tether impermeable. In one embodiment, the impermeable protective barrier material may coat a portion of the outer membrane of the capsule. Exemplary protective barrier material includes polyethylene oxides, polypropylene oxides, silicon, hydrogels, and derivatives and mixtures thereof. It should be appreciated that the semipermeable membrane may have alternative shapes that will accommodate the cells such as, for example, a hollow rod, sack, or multiple fibers.

The outer membrane may be a polymer material and may include a surfactant, an anti-inflammatory agent, angiogenic factors, and/or an anti-oxidant. The specific type of polymer, surfactant, or other additive will depend on the material to be encapsulated and the configuration of the extrusion apparatus. Exemplary anti-inflammatory agents include corticoids such as cortisone and ACTH, dexamethasone, cortisol, interleukin-1 and its receptor antagonists, and antibodies to TGF-β, to interleukin-1 (IL-1), and to interferon-gamma. Exemplary surfactants include Triton-X 100 from Sigma Chemicals, and Pluronics P65, P32, and P18. Exemplary anti-oxidants include vitamin C (ascorbic acid) and vitamin E. Exemplary angiogenic factors include fibroblast growth factor and nerve growth factor.

In the event that the supply of active factors, e.g., cells secreting such factors, is spent, the vehicle can be removed and replaced. Retrieval of implanted vehicle 40 can be accomplished by pulling it out of the treatment site by its tether 44. One way to effect removal is to use a pair of forceps after exposing the tether 44 by removal of the cap 62. Cap 62 may be located directly under the patient's epithelial tissues. The vehicle 40 may be replaced with a new insert in the event that additional therapy is required. Cells encapsulated within capsule 42 (FIG. 4) can also be retrieved if the cells cease to produce the biologically active factor, expire, or are no longer needed to correct the particular dysfunction.

The permeable portion (e.g., capsule 42) of vehicle 40 is implanted at or near the target treatment site 12, while the impermeable portion (e.g., tether 42) confines the neuroactive factor to within the boundaries of the insert. The permeable portion includes a polymeric material having pores of a particular size (i.e., having a particular molecular weight cut-off) that excludes some molecules from passage therethrough, while permitting the passage of others. In this way, the diffusion of neurotransmitter from the insert to the treatment site is allowed, while the passage of larger deleterious elements such as viruses, Clq component complement, and various proteases is effectively barred. For example, vehicles with pores having a molecular weight exclusion of from about 50 kD to about 300 kD are useful, with those having pores with a molecular weight cut off of from about 25 kD to about 200 kD being particularly preferred.

The vehicle may be composed of any biocompatible material having the desired pore size and being composed of materials which do not limit the activity of the substance embedded therein. Hydrophilic matrices such as hydrogels (e.g., hydroxyethyl methacrylate, polyanhydrides, polyvinyl alcohol, and polyvinyl pyrrolidone) and hydrophobic matrices such as ethylene vinyl acetate are particularly useful.

The vehicle 40 can provide any biologically active factor which will satisfy the subject deficiency or remedy the dysfunction. These include gamma aminobutyric acid, serotonin, acetylcholine, epinephrine, norepinephrine, dopamine, enkephalins, and endorphins. Alternatively, the device may provide an active analog, active fragment, or active derivative of the neuroactive factor, or may include a precursor which, after processing, provides the same activity as the factor in the appropriate in vivo location. The device may further include an agonist of the factor. Other agents may include insulin, Factor VIII, trophic factors such as, erythropoeitin and growth hormone, biological response modifiers, such as lymphokines and cytokines, enzymes, and antibodies from antibody-secreting cells. In addition, the capsule may contain multiple cell-types and cells, tissue, or other appropriate substance.

An exemplary form of the vehicle 40 is a smooth, seamless vehicle manufactured by coextrusion of a polymeric casting solution and a cell solution. In this approach a multi-bore extrusion nozzle is used with the polymeric solution extruded from the outer bore and the cell suspension coextruded from an inner bore. In addition to containing cells of tissue of the type described above, the cell suspension may include nutrients, such as fetal bovine, equine or porcine serum.

Any cells which secrete the biologically active factor that is therapeutic to the subject malady may be incorporated into the system of the invention. For example, the cells may be any which naturally produce a neurotransmitter, such as neurons. Such cells are useful because they are able to respond to the general environment by producing neurotransmitter as it is needed. Further, cells can be obtained from a number of sources such as body organs which normally secrete a particular factor in vivo. For example, tissues of the embryonic ventral mesencephalon and adrenal medulla (chromaffin cells) which normally produce dopamine can be used. These tissues may be an allograft or a xenograft. Alternatively, the cell may be derived from various cultured cell lines, such as PC12.

Where the intended transplantation site is a CNS pain modulatory region with the end goal of decreasing nociception, the encapsulation of adrenal medullary tissue and more particularly, chromaffin cells, of the adrenal medulla, may be desirable. In addition to dopamine, chromaffin cells release several other neuroactive and substances, including catecholamines and opioid peptides, which can reduce pain sensitivity when administered directly into the spinal cord. (Sagen et al. (1991) *J. Neurochem* 56: 623–627; Sagen et al. (1986) *Brain Res.* 384: 189–194; and Sagen et al. (1990) *Pain* 42: 69–79, incorporated by reference herein).

Various "growth factors" having the ability to stimulate cell growth, differentiation, and/or factor secretion may be co-implanted with the active factor-secreting cells to insure successful delivery of the desired agent or factor to the treatment site. These growth factors may be specific for a cell type or have a generalized effect on a number of different tissues. In the case of neurotransmitter-producing cells such as neurons, growth factors can act to maintain neurotransmitter production, as well as to promote cell maintenance and growth. Alternatively, growth factors may maintain nerve cells in a differentiated state. Useful cell growth factors include nerve growth factor (NGF), an array of fibroblast growth factors (FGF), platelet-derived growth factor (PDGF), brain-derived neuroprophic factor (BDNF), and epidermal growth factor (EGF), and ciliary growth factor, among many. In addition, effectors of various membrane receptors such as glutamate and nicotine may also be useful.

In addition, any cell which secretes a precursor, agonist, active analog, or active fragment of a desired biologically active factor or growth factor having similar therapeutic activity can also be used. For example, cells which elicit L-dopa, a precursor of dopamine, or bromocriptine, a dopamine agonist may be used in the treatment of Parkinson's disease.

Further, any cells which have been genetically engineered to express a desired neuroactive factor, growth factor, or their agonists, precursors, derivatives, analogs, or fragments thereof, or other active factors having similar effector activities are also useful in practicing this invention. Thus, in such an approach, the gene which encodes the neuroactive factor, or its analog or precursor is either isolated from a cell line or constructed by DNA manipulation. The gene can then be incorporated into a plasmid which, in turn, is transfected into a cell, such as a fibroblast, for expression. (See, e.g., Sambrook et al., *Molecular Cloning* (1989), herein incorporated by reference for further discussion of cloning vehicles and gene manipulation procedures.) The cells which express the biologically active factor or factor can be grown in vitro until a suitable density is achieved.

Alternatively, growth factor-producing cells such as hippocampal cells or fibroblasts engineered to produce NGF (see e.g., Rosenberg et al. (1988) Science 242:1575–1578) may be encapsulated and implanted in proximity to the factor-secreting cells as described above.

By the term "biocompatibility" is meant that the functioning of the vehicle is not impeded by the various protective systems of the host. This includes a failure to elicit a detrimental foreign body/fibrosis response. The vehicle is also preferably substantially free of local cytotoxic effects, i.e., free of leachable pyrogens. In a preferred form, a seamless tethered capsule is used as the vehicle. In embodiments employing seamed capsules, the number and size of the seams are preferably minimized, and the vehicle has smooth surfaces without edges or villi. Although many forms of tether may be attached, preferred tethers are continuous with the capsule.

The system of the invention, useful for practicing the inventive method as described above, includes a cannula, at least one obturator, and a biological vehicle. Each of these is substantially as described above.

In one particular aspect of the invention, a method of treating Parkinson's disease by neural implant has been developed. The cells can be cells from primary cultures or cell lines that secrete dopamine and other active factors. Typical factor-secreting primary cells include adrenal chromaffin cells, and neurons from the fetal substantia nigra. A suitable cell line is the PC12 line. Additionally, genetically engineered fibroblasts or other cell types may be used. Prior to use, cells are cultured by standard techniques appropriate for the cell type used.

In another aspect of the invention, a method and system for administering antinociceptive agents to alleviate pain have been developed. The encapsulated material can be tissue or cells able to secrete such antinociceptive agents as catecholamines and opioid peptides. Typically, the encapsulated material can be tissue of the adrenal medulla, or more particularly, adrenal medulla chromaffin cells. Additionally, genetically engineered cell lines or naturally other naturally occuring cell lines able to secrete at least one pain reducing agent such as a catecholamine, opioid peptide, or agonist analogs thereof, can be used.

In one preferred embodiment, the capsule used is a thermoplastic PAN/PVC capsule with a liquid and cell core, having a wall thickness of greater than 25 microns. The core may also contain a hydrogel matrix or the like. The hydrogel matrix may be any commercially available three-dimensional network of hydrophilic polymers that are either covalently or ionically cross-linked. Any method of thermoplastic capsule preparation may be used, including hollow fiber preparation followed by filling with the cells and plugging and sealing using heat sealing. Alternatively, the capsules can be formed by coextrusion through a multi-lumen spinneret.

The inclusion of a tether to the biocompatible vehicle should not affect capsule functioning or its biocompatibility. The entire length of the exemplary vehicle, including the tether, typically is 8–10 cm. Methods of tether manufacture include coextrusion through a multi-lumen spinneret. Other methods include the addition of a biocompatible suture protruding from the sealed capsule. Another form includes a hollow immunoisolatory fiber of 80–100 mm in length containing, at one end, a cell growth chamber of 10–20 mm with an internal plug. To produce a sturdy, non-porous tether, the remainder of the fiber is dipped in a potting elastomer, such as polyurethane or polysilicon, preferably prior to loading the cells. In other forms, elastomeric tubing may be attached to the capsule.

Although illustrated specifically for cranial insertion in FIG. 4, the vehicles of the present invention can also be inserted into other regions of the body. For example, for pain relief applications the vehicles can be inserted into the sacral/lumbar regions of the spine to provide encapsulated cells such as adrenal chromaffin cells which secrete enkephalins and/or catecholamines.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A system for delivering a biologically active factor to a selected treatment site in a subject, comprising:

i) a single cannula adapted for penetration through tissue into a selected position in proximity with the treatment site, having a bore with a substantially smooth interior surface running axially therethrough through which a vehicle may slidably move, an open, proximal end into which the vehicle may be slidably inserted and a distal end having an opening through which the vehicle may slidably move wherein the external diameter and bore diameter are tapered toward the distal tip;

ii) an obturator disposable within the cannula to prevent tissue material from entering the distal end of the cannula when it is inserted into tissue;

iii) a vehicle which encapsulates the biologically active factor, the vehicle having an outer surface which comprises a biocompatible semipermeable outer membrane through which the biologically active factor may be released into the selected treatment site, and a shape which enables slidable insertion into the proximal end of the cannula, slidable movement along the bore of the cannula, slidable passage through the distal end of the cannula by removal of the cannula from the proximity of the treatment site; and iv) a pusher disposable within the cannula to engage the outer surface of the vehicle, to slidably move the vehicle through the bore, and to hold the vehicle in place at the selected treatment site when the cannula is removed from the proximity of the treatment site, the pusher being removable after the vehicle is positioned at the treatment site.

2. The system of claim 1, further comprising:

i) a guidance needle having a lumen running axially therethrough and being insertable into proximity with the treatment site;

ii) a guidewire insertable into proximity with the treatment site and able to pass completely through the lumen of the guidance needle;

wherein the cannula is adapted to receive the guidewire and wherein the lumen of the guidance needle has a first open end for receiving the guidewire, and a second open end for passage of the guidewire to the treatment site, the guidance needle being fully removable after insertion of the guidewire to the treatment site without disturbing the proximity of the guidewire to the treatment site, and the guidewire being able to guide the insertion of the cannula to the treatment site.

3. The system of claim 2, further comprising at least one dilator disposable along the guidewire to enlarge a pathway through which the cannula is inserted, the dilator having a dilator bore running axially therethrough and able to pass the guidewire therein.

4. The system of claim 3, wherein the guidance needle has a beveled, curved tip.

5. The system of claim 2, further comprising at least one obturator for insertion within and along the lumen of the guidance needle to prevent backfill of materials into the guidance needle during insertion of the guidance needle, the obturator being fully removable after insertion of the guidance needle into proximity with the treatment site.

6. The system of claim 1, wherein at least a portion of the proximal end of the cannula is transparent to permit monitoring the progress of the vehicle during insertion into the cannula and during passage through the transparent portion of the cannula.

7. The system of claim 1, wherein the distal end of the cannula is rounded to reduce ancillary tissue damage, and wherein the active factor comprises at least one neuroactive factor selected from the group consisting of peptide neurotransmitters, growth factors, trophic factors, catecholamines, opioid peptides and hormones.

8. The system of claim 1, wherein the system is adapted for delivering the vehicle into a human spinal region, and wherein the vehicle releases at least one antinociceptive agent useful in a treatment for pain relief.

9. The system of claim 1, wherein the vehicle encapsulates cells that secrete the biologically active factor.

10. The system of claim 9, wherein the encapsulated cells comprise adrenal medullary chromaffin cells.

11. The system of claim 9, wherein the distal end of the cannula is rounded to reduce ancillary tissue damage, and wherein the active factor comprises a neuroactive factor selected from the group consisting of peptide neurotransmitters, growth factors, trophic factors, catecholamines, opioid peptides and hormones.

12. The system of claim 1, wherein the vehicle further comprises an impermeable protective barrier material which coats a portion of the outer membrane.

13. The system of claim 1, wherein the cannula is constructed from material comprising a low friction polymer.

14. The system of claim 13, wherein the polymer comprises polytetrafluoroethylene.

15. The system of claim 1, wherein the active factor comprises at least one antinociceptive agent useful in a treatment for pain relief.

16. The system of claim 1, wherein the cannula is flexible for the delivery of the vehicle through a curved pathway.

17. A method for delivering a biologically active factor to a selected treatment site in a subject, comprising:

i) surgically opening an insertion site located near the selected treatment site;

ii) inserting a single cannula adapted for penetration through tissue and an obturator disposed therein into the insertion site and placing the distal end of the cannula at a selected position in proximity with the treatment site, the cannula having a bore with a substantially smooth surface running axially therethrough through which a vehicle may slidably move, an open, proximal end into which the vehicle may be slidably inserted and a distal end having an opening through which the vehicle may slidably move wherein the external diameter an bore diameter are tapered toward the distal tip;

iii) removing the obturator from the cannula;

iv) introducing within the bore of the cannula a vehicle which encapsulates the biologically active factor, the vehicle having an outer surface which comprises a biocompatible semipermeable outer membrane through which the biologically active factor may be released into the selected treatment site, and a shape which enables slidable insertion into the proximal end of the cannula, slidable movement along the bore of the cannula, slidable passage through the distal end of the cannula by removal of the cannula from the proximity of the treatment site;

v) delivering the vehicle to the distal end of the cannula with a pusher disposable within the cannula to engage the outer surface of the vehicle, to slidably move the vehicle through the bore, and to hold the vehicle in place at the selected treatment site when the cannula is removed from the proximity of the treatment site;

vi) removing the cannula from the tissue, while leaving the vehicle inserted at the treatment site; and vii) removing the pusher from the tissue.

18. The method of claim 17, further comprising before a step of inserting the cannula, i) inserting a guidance needle having a lumen running axially therethrough into proximity with the treatment site;

ii) inserting a guidewire through the lumen of the inserted needle and into proximity with the treatment site, the guidewire able to pass completely through the lumen of the guidance needle; and iii) removing the guidance needle from the treatment site without disturbing the proximity of the guidewire to the treatment site; wherein the cannula is adapted to receive the guidewire and wherein the lumen of the guidance needle has a first open end for receiving the guidewire, and a second open end for passage of the guidewire to the treatment site, the guidance needle being fully removable after insertion of the guidewire to the treatment site without disturbing the proximity of the guidewire to the treatment site, and the guidewire being able to guide the insertion of the cannula to the treatment site.

19. The method of claim 18, further comprising disposing, after removing the guidance needle, at least one dilator along the guidewire and towards the treatment site to enlarge a pathway through which the cannula is inserted, the dilator having a dilator bore running axially therethrough and able to pass the guidewire therein, the dilator being removed before the cannula is removed.

20. The method of claim 18, further comprising, before a step of inserting the guidewire, disposing at least one obturator in the lumen of the guidance needle, the obturator of the type designed for insertion within and along the lumen of the guidance needle to prevent backfill of materials into the guidance needle during insertion of the guidance needle into proximity with the treatment site, the obturator being removed before the guidewire is inserted.

* * * * *